United States Patent
Sato

(10) Patent No.: US 7,998,929 B2
(45) Date of Patent: Aug. 16, 2011

(54) SOLUTION PREPARATIONS STABILIZED OVER LONG TIME

(75) Inventor: Yasushi Sato, Tokyo (JP)

(73) Assignee: Chugai Seikyaku Kabushiki Kaisha, Tokyo (JP)

( * ) Notice: Subject to any disclaimer, the term of this patent is extended or adjusted under 35 U.S.C. 154(b) by 458 days.

(21) Appl. No.: 10/362,921

(22) PCT Filed: Sep. 3, 2001

(86) PCT No.: PCT/JP01/07600
§ 371 (c)(1),
(2), (4) Date: Feb. 27, 2003

(87) PCT Pub. No.: WO02/17957
PCT Pub. Date: Mar. 17, 2002

(65) Prior Publication Data
US 2004/0037803 A1     Feb. 26, 2004

(30) Foreign Application Priority Data

Sep. 1, 2000    (JP) ................. 2000/266095

(51) Int. Cl.
*A61K 38/00*    (2006.01)
*A61K 38/18*    (2006.01)
*A61M 5/00*    (2006.01)
*B65D 69/00*    (2006.01)

(52) U.S. Cl. ....... 514/7.9; 514/7.6; 424/198.1; 604/181; 604/187; 604/188; 604/232; 206/571

(58) Field of Classification Search .................. None
See application file for complete search history.

(56) References Cited

U.S. PATENT DOCUMENTS

| | | | | |
|---|---|---|---|---|
| 5,358,708 A | * | 10/1994 | Patel | 424/85.1 |
| 5,534,269 A | * | 7/1996 | Igari et al. | 424/489 |
| 5,607,400 A | * | 3/1997 | Thibault et al. | 604/230 |
| 5,919,443 A | | 7/1999 | Michaelis et al. | |
| 5,919,757 A | * | 7/1999 | Michaelis et al. | 514/8 |
| 6,646,110 B2 | * | 11/2003 | Nissen et al. | 530/397 |
| 6,776,983 B1 | * | 8/2004 | Sumida et al. | 424/85.1 |
| 6,908,610 B1 | * | 6/2005 | Sato | 424/85.1 |

FOREIGN PATENT DOCUMENTS

| | | |
|---|---|---|
| EP | 1 060 746 A1 | 12/2000 |
| EP | 1 197 221 A1 | 4/2002 |
| GB | 2 193 631 A | 2/1988 |
| JP | 63-146829 A | 6/1988 |
| JP | 2577744 B2 | 11/1996 |
| WO | 92/15614 A1 | 9/1992 |
| WO | WO 92/15614 * | 9/1992 |
| WO | WO-93/03745 A1 | 3/1993 |
| WO | WO99/44630 * | 9/1999 |
| WO | WO99/44630 A1 | 9/1999 |
| WO | WO 00/51629 A1 | 9/2000 |

OTHER PUBLICATIONS

Oh-eda et al., J. Biol. Chem., 1990, vol. 265, pp. 11432-11435.*

* cited by examiner

*Primary Examiner* — Elizabeth C Kemmerer
*Assistant Examiner* — Xiaozhen Xie
(74) *Attorney, Agent, or Firm* — Birch, Stewart, Kolasch & Birch, LLP

(57) ABSTRACT

A G-CSF solution formulation which is substantially free from proteins as a stabilizer but which contains at least one amino acid or a salt thereof as a stabilizer.

41 Claims, No Drawings

SOLUTION PREPARATIONS STABILIZED OVER LONG TIME

FIELD OF THE INVENTION

The present invention relates to G-CSF (granulocyte colony-stimulating factor) solution formulations, and particularly stabilized G-CSF formulations showing low loss of active ingredients and low production of oxidized G-CSF at methionine residues even after long-term storage.

BACKGROUND ART

G-CSF is a glycoprotein having a molecular weight of about 20,000 and acting on precursor cells of neutrophils to promote their proliferation and differentiation to maturation.

Since we obtained high-purity human G-CSF by culturing a cell line collected from tumor cells of a patient with cancer of the floor of the mouth, the human G-CSF gene was successfully cloned and, at present, recombinant human G-CSF can be produced in mass in microorganisms or animal cells by genetic engineering techniques. We also succeeded in formulating this purified G-CSF into pharmaceutical products supplied to the market as antiinfection agents (Japanese Patent No. 2116515).

G-CSF is used in a very small amount, i.e., a formulation containing 0.1-1000 µg (preferably 5-500 µg) of G-CSF is normally administered once to seven times per week per adult. However, this G-CSF tends to be adsorbed to the walls of ampules for injection, syringes or the like. Moreover, G-CSF is unstable and susceptible to extrinsic factors such as temperature, humidity, oxygen, UV rays or the like to undergo physical or chemical changes including association, polymerization or oxidation, resulting in great loss of activity.

In order to prevent these influences, various formulation designs have been proposed mainly in dosage forms of freeze-dried formulations. For example, formulations containing at least one member selected from the group consisting of (a) at least one amino acid selected from threonine, tryptophan, lysine, hydroxylysine, histidine, arginine, cysteine, cystine and methionine; (b) at least one sulfur-containing reducing agent; or (c) at least one antioxidant were proposed (Japanese Patent No. 2577744). G-CSF formulations containing a surfactant such as a Polysorbate as a stabilizer were also proposed (JP-A-63-146826).

Freeze-dried G-CSF formulations containing maltose, raffinose, sucrose, trehalose or an aminosugar were also reported (JP-A-8-504784).

However, freeze-drying processes entail an increase in production costs on a commercial basis as well as an increase in the danger resulting from mechanical failure. Moreover, freeze-dried formulations had the problem that they must be dissolved in pure water (sterilized water for injection) before use.

Some products currently on the market contain a protein commonly used as a stabilizer such as human serum albumin or purified gelatin for controlling such chemical or physical changes. However, the addition of a protein as a stabilizer involved problems such as the necessity of a very complicated process for removing contamination with viruses.

However, production of oxidized G-CSF at methionine residues increases in the absence of such a protein, leading to deterioration.

For the reasons described above, there are demands for G-CSF solution formulations alternative to freeze-dried formulations, which are free from proteins as stabilizers and stable even after long-term storage.

DISCLOSURE OF THE INVENTION

As a result of careful studies to achieve the above object, we accomplished the present invention on the basis of the finding that a G-CSF solution formulation showing a high residual G-CSF level and low production of oxidized G-CSF at methionine residues even after long-term storage can be obtained by adding specific amino acids in combination as stabilizers.

Accordingly, the present invention provides a G-CSF solution formulation which is substantially free from proteins as a stabilizer but which contains at least one amino acid or a salt thereof as a stabilizer.

The present invention also provides the above G-CSF solution formulation wherein the amino acid is one or more members selected from glycine, sodium glutamate, arginine and histidine or a salt thereof.

The present invention also provides the above G-CSF solution formulation wherein the amino acid is one or more members selected from arginine and histidine or a salt thereof.

The present invention also provides the above G-CSF solution formulation wherein the amino acid is histidine or a salt thereof.

The present invention also provides the above G-CSF solution formulation further containing methionine.

The present invention also provides the above G-CSF solution formulation wherein the amino acid is contained in an amount of 0.01-10% by weight.

The present invention also provides the above G-CSF solution formulation wherein histidine or a salt thereof is contained in an amount of 0.01-10% by weight.

The present invention also provides the above G-CSF solution formulation further-containing mannitol and/or sodium chloride.

The present invention also provides the above G-CSF solution formulation further containing a surfactant.

The present invention also provides the above G-CSF solution formulation wherein the above surfactant is a polyoxyethylene sorbitan alkyl ester.

The present invention also provides the above G-CSF solution formulation wherein the above surfactant is Polysorbate 20 and/or 80.

The present invention also provides the above G-CSF solution formulation having a pH of 5-7.

The present invention also provides the above G-CSF solution formulation having a pH of 5.5-6.8.

The present invention also provides the above G-CSF solution formulation wherein G-CSF is produced from CHO cells.

The present invention also provides the above G-CSF formulation in the form of a vial formulation or a prefilled syringe formulation.

The present invention also provides a stable G-CSF solution formulation having a residual G-CSF level of 90% or more after accelerated testing at 40° C. for 2 weeks or a residual G-CSF level of 97% or more after stability testing at 25° C. for 6 months or a residual G-CSF level of 97% or more after stability testing at 10° C. for 1 year and oxidized G-CSF at methionine residues in a content of 1% or less after accelerated testing at 40° C. for 2 weeks.

The present invention also provides the above stable G-CSF solution formulation substantially free from oxidized G-CSF at methionine residues. The expression "substantially free from oxidized G-CSF at methionine residues" here means that the oxidized G-CSF at methionine residues is below detection limit.

The present invention also provides a method for stabilizing a G-CSF solution formulation, comprising adding at least one amino acid or a salt thereof as a stabilizer in substantial absence of added protein as a stabilizer.

The present invention also provides use of at least one amino acid or a salt thereof for the preparation of a stabilized G-CSF solution formulation.

The solution formulations of the present invention refer to formulations involving no freeze-drying step in the preparation process and suitable for long-term storage as solutions.

THE MOST PREFERRED EMBODIMENTS OF THE INVENTION

The G-CSF used in solution formulations of the present invention may be any high-purity human G-CSF. Specifically, it may be derived from natural sources or genetically engineered so far as it has substantially the same biological activity as that of mammalian, particularly human G-CSF. Genetically engineered G-CSF may have the same amino acid sequence as that of natural G-CSF or may contain deletion, substitution or addition of one or more amino acids in the above amino acid sequence while maintaining the above biological activity. The G-CSF in the present invention may be prepared by any process, e.g., it may be extracted, isolated and purified by various techniques from cultures of a human tumor cell line or may be produced by genetic engineering techniques in bacterial cells such as $E.\ coli$; yeast cells; animal culture cells such as Chinese hamster ovary (CHO), C127 or COS cells and then extracted, isolated and purified by various techniques. G-CSF is preferably produced by genetic recombination in $E.\ coli$, yeast or CHO cells, most preferably by genetic recombination in CHO cells. G-CSF chemically modified with PEG or the like is also included (see International Publication No. WO90/12874).

Preferably, G-CSF solution formulations of the present invention are substantially free from proteins such as human serum albumin or purified gelatin as stabilizers.

G-CSF solution formulations of the present invention contain at least one amino acid or a salt thereof as a stabilizer. The amino acid is preferably one or more members selected from glycine, sodium glutamate, arginine and histidine or a salt thereof, more preferably one or more members selected from arginine and histidine or a salt thereof, most preferably histidine or a salt thereof.

Amino acids used in the present invention include free amino acids and salts thereof such as sodium salts, potassium salts and hydrochlorides. Formulations of the present invention may contain D-, L- and DL-isomers of these amino acids, more preferably L-isomers and salts thereof.

The amount of amino acids to be added to formulations of the present invention can be determined in a preferred range using the test method described below depending on the type of the amino acid used. They are typically added in an amount of 0.001-10% by weight, preferably 0.01-5% by weight, more preferably 0.1-3% by weight. Histidine or a salt thereof is typically added in an amount of 0.01-10% by weight, preferably 0.05-3% by weight, more preferably 0.1-2% by weight. Histidine hydrochloride showed a very high residual G-CSF level in the tested range of 0.1-1.6% by weight and the highest level at 0.4% by weight in accelerated testing at 40° C. for 2 weeks.

G-CSF solution formulations of the present invention preferably contain methionine. Methionine is preferably added in an amount of 0.001-5% by weight, more preferably 0.01-1% by weight, most preferably 0.1% by weight. It was observed that the content of oxidized G-CSF at methionine residues could be lowered below detection limit by adding methionine. Without wishing to be bound to any specific theory, we supposed that the added methionine was oxidized in place of methionine residues of G-CSF, thereby decreasing the production of oxidized G-CSF at methionine residues.

Formulations of the present invention may contain isotonizing agents, e.g., polyethylene glycol; sugars such as dextran, mannitol, sorbitol, inositol, glucose, fructose, lactose, xylose, mannose, maltose, sucrose and raffinose; and inorganic salts such as sodium chloride and potassium chloride, preferably mannitol or sodium chloride, especially mannitol. The amount of sugars such as mannitol to be added to formulations is 0.1-10% by weight, more preferably 0.5-6% by weight. The amount of inorganic salts such as sodium chloride to be added to formulations is 20-200 mM, preferably 50-150 mM.

Formulations of the present invention may further contain surfactants. Typical examples of surfactants include:

nonionic surfactants, e.g., sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6-18;

anionic surfactants, e.g., alkyl sulfates having a C10-18 alkyl group such as sodium cetyl sulfate, sodium lauryl sulfate, sodium oleyl sulfate; polyoxyethylene alkyl ether sulfates having an average ethylene oxide mole number of 2-4 and a C10-18 alkyl group such as sodium polyoxyethylene lauryl sulfate; alkyl sulfosuccinic acid ester salts having a C8-18 alkyl group such as sodium laurylsulfosuccinate; and natural surfactants, e.g., lecithin; glycerophospholipids; sphingophospholipids such as sphingomyelin; sucrose fatty acid esters of C12-18 fatty acids. One or more of these surfactants may be added in combination to formulations of the present invention.

Preferred surfactants are polyoxyethylene sorbitan fatty acid esters, more preferably Polysorbates 20, 21, 40, 60, 65, 80, 81, 85, most preferably Polysorbates 20 and 80.

The amount of surfactants added to G-CSF-containing formulations of the present invention is typically 0.0001-10 parts by weight per part by weight of G-CSF, preferably 0.01-5 parts by weight per part by weight of G-CSF, most preferably 0.2-2 parts by weight per part by weight of G-CSF. Specifically, the amount of surfactants to be added can be appropriately selected within 0.0001-0.5% by weight.

G-CSF solution formulations of the present invention preferably have a pH of 5-7, more preferably 5.5-6.8, still more preferably 6-6.7, most preferably 6.5.

G-CSF solution formulations of the present invention may further contain diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate, sodium metaphosphate. Other components commonly added may also be contained, e.g., inorganic salts such as sodium chloride, potassium chloride, calcium chloride, sodium phosphate, potassium phosphate, sodium bicarbonate; and organic salts such as sodium citrate, potassium citrate, sodium acetate.

Solution formulations of the present invention can be prepared by dissolving these components in an aqueous buffer known in the art of solution formulations such as phosphate buffers (preferably sodium monohydrogen phosphate-sodium dihydrogen phosphate system) and/or citrate buffers (preferably sodium citrate buffer).

Stabilized G-CSF-containing solution formulations of the present invention are typically administered via parenteral routes such as injection (subcutaneous, intravenous or intramuscular injection) or percutaneous, mucosal, nasal or pulmonary administration, but may also be orally administered.

G-CSF solution formulations of the present invention are typically packed in a sealed and sterilized plastic or glass container. The container can be supplied in a unit dosage form such as an ampule, vial or disposable syringe or in a bulk form such as an injection bag or bottle.

The amount of G-CSF contained in formulations of the present invention can be determined depending on the type of the disease to be treated, the severity of the disease, the age of the patient or other factors, but typically ranges from 1 to 1000 μg/mL, preferably 10 to 800 μg/mL, more preferably 50 to 500 μg/mL expressed as a final dosage level.

Formulations of the present invention are clinically very useful as they were found to improve protective functions based on immune response such as resistance of the patient or activity when they were coadministered with such drugs as antibiotics, antibacterial agents or anticancer agents in the chemotherapy of infectious diseases or cancer. Therefore, formulations of the present invention can be administered in combination with these drugs.

As shown in the examples below, G-CSF solution formulations of the present invention show very good residual G-CSF levels after accelerated testing at 40° C. for 2 weeks. Moreover, little production of oxidized G-CSF at methionine residues was observed after accelerated testing at 40° C. for 2 weeks.

G-CSF solution formulations of the present invention have a residual G-CSF level of 90% or more, preferably 93% or more, most preferably 95% or more after accelerated testing at 40° C. for 2 weeks, or a residual G-CSF level of 97% or more after stability testing at 25° C. for 6 months, or a residual G-CSF level of 97% or more after stability testing at 10° C. for 1 year and oxidized G-CSF at methionine residues in a content of 1% or less, preferably below detection limit after accelerated testing at 40° C. for 2 weeks, showing that they are very stable as compared with known G-CSF formulations.

During studies of the present invention, an increase in oxidized G-CSF at methionine residues was observed under some conditions of containers such as vials and syringes containing solution formulations (e.g., variation among production lots), especially in syringe-type containers when histidine was added. This production of oxidized G-CSF at methionine residues was almost completely inhibited by the addition of methionine. Thus, formulations having long-term stability which shows a very high residual G-CSF level and a low content of oxidized G-CSF at methionine residues can be supplied as prefilled syringe formulations by adding an amino acid such as histidine and an agent for inhibiting the production of oxidized G-CSF at methionine residues such as methionine or a known antioxidant.

INDUSTRIAL APPLICABILITY

G-CSF solution formulations of the present invention are stable formulations showing a very high residual G-CSF level and capable of almost completely inhibiting the production of oxidized G-CSF at methionine residues irrespective of the type of isotonizing agent or the form of container after both short-term accelerated testing and long-term storage.

The following examples further illustrate the present invention without, however, limiting the scope of the invention thereto. Various changes and modifications can be made by those skilled in the art on the basis of the description of the invention, and such changes and modifications are also included in the present invention.

EXAMPLES

Example 1

Effect of Various Amino Acids on Stability

Formulated solutions were prepared according to the recipes shown in Table 1 by mixing 250 μg/mL of G-CSF, the indicated concentration (% by weight per volume (w/v)) of each amino acid as listed, and 0.01% (w/v) of polysorbate 20 at pH 6.5. The formulated solutions were aseptically filtered and aseptically filled into glass vials in a volume of 1 mL, the vials being then capped.

TABLE 1

| Sample No. | G-CSF (μg/mL) | Amino acid added | (%) | Polysorbate-20 (%) | pH |
|---|---|---|---|---|---|
| 1 | 250 | Glycine | 5 | 0.01 | 6.5 |
| 2 | 250 | Alanine | 4 | 0.01 | 6.5 |
| 3 | 250 | Proline | 0.6 | 0.01 | 6.5 |
| 4 | 250 | Leucine | 0.32 | 0.01 | 6.5 |
| 5 | 250 | Sodium glutamate | 0.32 | 0.01 | 6.5 |
| 6 | 250 | Hydroxyproline | 0.08 | 0.01 | 6.5 |
| 7 | 250 | Arginine hydrochloride | 0.4 | 0.01 | 6.5 |
| 8 | 250 | Lysine hydrochloride | 1 | 0.01 | 6.5 |
| 9 | 250 | Histidine hydrochloride | 0.4 | 0.01 | 6.5 |

The G-CSF formulations shown in Table 1 thus obtained by septic preparation and filtration were subjected to acceleration in an incubator at 40° C. for 2 weeks. Samples accelerated at 40° C. for 2 weeks and those not accelerated were assayed to calculate the residual level (%) after acceleration at 40° C. for 2 weeks using evaluation method 1 below.

Evaluation method 1

The G-CSF content was determined by reverse phase high-speed liquid chromatography using a C4 reverse phase column (4.6 mm×250 mm, 300 angstroms) with a mobile phase consisting of pure water, acetonitrile and trifluoroacetic acid. The amount equivalent to 5 μg of G-CSF was injected and G-CSF was eluted with an acetonitrile gradient and spectroscopically detected at a wavelength of 215 nm to determine the G-CSF content.

The G-CSF content determined by this method was used to calculate the residual level (%) after acceleration at 40° C. for 2 weeks according to the following equation.

$$\text{Residual level}(\%) = \frac{(G\text{-}CSF \text{ content in accelerated sample})}{(G\text{-}CSF \text{ content in unaccelerated sample})} \times 100$$

The results are shown in Table 2 below.

TABLE 2

| Sample No. | Amino acid | Residual level after acceleration at 40° C. for 2 weeks (%) |
|---|---|---|
| 1 | Glycine | 92.3 |
| 2 | Alanine | 89.6 |
| 3 | Proline | 87.1 |
| 4 | Leucine | 83.7 |
| 5 | Sodium glutamate | 90.2 |
| 6 | Hydroxyproline | 89.1 |
| 7 | Arginine hydrochloride | 96.3 |
| 8 | Lysine hydrochloride | 85.5 |
| 9 | Histidine hydrochloride | 97.0 |

Good residual levels were observed after acceleration at 40° C. for 2 weeks by adding glycine, sodium glutamate, arginine hydrochloride or histidine hydrochloride, and the residual level was remarkably improved especially by adding arginine hydrochloride or histidine hydrochloride.

Example 2

Effect of Addition of Methionine on the Production of Oxidized G-CSF

Formulated solutions were prepared according to the recipes shown in Table 3 by mixing 100 μg/mL of G-CSF, each concentration (% by weight per volume) of methionine as listed, and 0.01% (w/v) of polysorbate 20 at pH 6.5. The formulated solutions were aseptically filtered and aseptically filled into glass vials in a volume of 1 mL, the vials being then capped.

TABLE 3

| Sample No. | G-CSF (μg/mL) | Met (%) | Polysorbate-20 (%) | pH |
|---|---|---|---|---|
| 10 | 100 | 0 | 0.01 | 6.5 |
| 11 | 100 | 0.1 | 0.01 | 6.5 |

Met: Methionine.

The G-CSF formulations shown in Table 3 thus obtained by aseptic preparation and filtration were stored in an incubator at 25° C. for 5 days, and then the contents of oxidized G-CSF were calculated using evaluation method 2 below.

Evaluation method 2

The G-CSF content was determined by reverse phase high-speed liquid chromatography using a C4 reverse phase column (4.6 mm×250 mm, 300 angstroms) with a mobile phase consisting of pure water, acetonitrile and trifluoroacetic acid. The amount equivalent to 5 μg of G-CSF was injected and G-CSF was eluted with an acetonitrile gradient and spectroscopically detected at a wavelength of 215 nm to determine the peak areas of oxidized G-CSF and intact G-CSF.

Each peak area determined by this method was used to calculate the oxidized G-CSF content (%) according to the following equation.

$$\text{Oxidized } G\text{-}CSF \text{ content }(\%) = 100 \times \frac{(\text{Peak area of oxidized } G\text{-}CSF)}{(\text{Peak area of oxidized } G\text{-}CSF) + (\text{Peak area of intact } G\text{-}CSF)}$$

The results are shown in Table 4 below.

TABLE 4

| Sample No. | G-CSF (μg/mL) | Met (%) | Oxidized G-CSF content (%) |
|---|---|---|---|
| 10 | 100 | 0 | 2.7 |
| 11 | 100 | 0.1 | N.D. |

Met: Methionine
N.D.: Not detected.

It was found that the production of oxidized G-CSF could be inhibited by the addition of methionine.

Example 3

Effect of Histidine Amounts on Stability

Formulated solutions were prepared according to the recipes shown in Table 5 by mixing 250 μg/ml of G-CSF, each concentration (% by weight per volume) of histidine hydrochloride as listed, 0.1% (w/v) of methionine and 0.01% (w/v) of Polysorbate 20 at pH 6.5. The formulated solutions were aseptically filtered and aseptically filled into glass vials in a volume of 1 mL, the vials being then capped.

TABLE 5

| Sample No. | G-CSF (μg/mL) | His (%) | Met (%) | NaCl (mM) | Polysorbate-20 (%) | pH |
|---|---|---|---|---|---|---|
| 12 | 250 | 0 | 0.1 | 100 | 0.01 | 6.5 |
| 13 | 250 | 0.1 | 0.1 | 100 | 0.01 | 6.5 |
| 14 | 250 | 0.4 | 0.1 | 100 | 0.01 | 6.5 |
| 15 | 250 | 0.8 | 0.1 | 100 | 0.01 | 6.5 |
| 16 | 250 | 1.6 | 0.1 | 100 | 0.01 | 6.5 |

His: expressed as histidine hydrochloride
Met: Methionine
NaCl: Sodium chloride.

The G-CSF formulations shown in Table 5 thus obtained by aseptic preparation and filtration were subjected to acceleration in an incubator at 40° C. for 2 weeks. Samples accelerated at 40° C. for 2 weeks and those not accelerated were assayed to calculate the residual level (%) after acceleration at 40° C. for 2 weeks using evaluation method 1 above.

The results are shown in Table 6 below.

TABLE 6

| Sample No. | His (%) | Residual level after acceleration at 40° C. for 2 weeks (%) |
|---|---|---|
| 12 | 0 | 85.5 |
| 13 | 0.1 | 97.2 |
| 14 | 0.4 | 99.1 |
| 15 | 0.8 | 97.6 |
| 16 | 1.6 | 98.1 |

His: expressed as histidine hydrochloride.

Thus, the addition of histidine could improve stability in short-term accelerated testing as shown by dramatic improvement in the residual level.

Oxidized G-CSF at methionine residues was below detection limit in all sample Nos. 12-16.

Example 4

Effect of the Form of Container on Stability

Formulated solutions were prepared according to the recipes shown in Table 7 by mixing 250 μg/ml of G-CSF, 0.4% (w/v) of histidine hydrochloride, 0.1% (w/v) of methionine and 0.01% (w/v) of Polysorbate 20 at pH 6.5. The formulated solutions were aseptically filtered and aseptically filled into containers of forms shown below in a volume of 1 mL, the containers being then capped.

TABLE 7

| Sample No. | G-CSF (μg/mL) | His (%) | Met (%) | NaCl (mM) | Polysorbate-20 (%) | pH | Form of container |
|---|---|---|---|---|---|---|---|
| 17 | 250 | 0 | 0 | 100 | 0.01 | 6.5 | Vial |
| 18 | 250 | 0 | 0 | 100 | 0.01 | 6.5 | Syringe |
| 19 | 250 | 0.4 | 0.1 | 100 | 0.01 | 6.5 | Vial |
| 20 | 250 | 0.4 | 0.1 | 100 | 0.01 | 6.5 | Syringe |

His: expressed as histidine hydrochloride
Met: Methionine
NaCl: Sodium chloride
Syringe: Glass syringe made by Becton Dickinson (Hypak SCF 1 mL long) filled with each of the formulated solutions above and sealed and capped with a plunger stopper made by Becton Dickinson (Hypak SCF).
Vial: Untreated white glass vial filled with the above formulated solutions and capped with a rubber stopper.

The G-CSF formulations shown in Table 7 thus obtained by aseptic preparation and filtration were subjected to acceleration in an incubator at 40° C. for 2 weeks. Samples accelerated at 40° C. for 2 weeks and those not accelerated were assayed to calculate the residual level (%) after acceleration at 40° C. for 2 weeks, after storage at 25° C. for 6 months or after storage at 10° C. for 1 year using evaluation method 1 above.

The results are shown in Table 8 below.

TABLE 8

| | | | Residual level (%) after | | |
|---|---|---|---|---|---|
| Sample No. | His (%) | Form of container | acceleration at 40° C., 2 weeks | storage at 25° C., 6 months | storage at 10° C., 1 year |
| 17 | 0 | Vial | 92.3 | 95.4 | 96.3 |
| 18 | 0 | Syringe | 90.8 | 93.1 | 93.3 |
| 19 | 0.4 | Vial | 98.0 | 97.7 | 98.1 |
| 20 | 0.4 | Syringe | 99.1 | 97.9 | 98.1 |

The effect of adding histidine was remarkable in not only short-term accelerated testing at 40° C. but also long-term storage testing at 25° C. and 10° C., showing that long-term storage stability of G-CSF formulations can be ensured by adding histidine. Oxidized G-CSF at methionine residues was below detection limit in both sample Nos. 19 and 20. It was concluded from these results that stabilized G-CSF formulations could be supplied irrespective of the form of container.

During this study, an increase in oxidized G-CSF at methionine residues was observed due to variation among production lots of vials or syringes containing solution formulations, especially in syringe-type containers when 0.4% histidine was added alone. This production of oxidized G-CSF at methionine residues fell below detection limit by the addition of 0.1% methionine.

Example 5

Effect of Isotonizing Agents on Stability

Formulated solutions were prepared according to the recipes shown in Table 9 by mixing 250 μg/ml of G-CSF, the indicated concentration of each isotonizing agent (sodium chloride or D-manitol), 0.4% (w/v) of histidine hydrochloride, 0.1% (w/v) of methionine and 0.01% (w/v) of Polysorbate 20 at pH 6.5. The formulated solutions were aseptically filtered and aseptically filled into glass vials in a volume of 1 mL, the vials being then capped.

TABLE 9

| Sample No. | G-CSF (μg/mL) | His (%) | Met (%) | Isotonizing agent | Polysorbate-20 (%) | pH |
|---|---|---|---|---|---|---|
| 21 | 250 | 0.4 | 0.1 | 100 mM NaCl | 0.01 | 6.5 |
| 22 | 250 | 0.4 | 0.1 | 2.5% mannitol | 0.01 | 6.5 |

His: expressed as histidine hydrochloride
Met: Methionine
NaCl: Sodium chloride

The G-CSF formulations shown in Table 9 thus obtained by aseptic preparation and filtration were subjected to acceleration in an incubator at 40° C. for 2 weeks. Samples accelerated at 40° C. for 2 weeks and those not accelerated were assayed to calculate the residual level (%) after storage at 25° C. for 4 months, at 25° C. for 6 months or at 10° C. for 1 year using evaluation method 1 above.

The results are shown in Table 10 below.

TABLE 10

| | | Residual level (%) after storage | | |
|---|---|---|---|---|
| Sample No. | Isotonizing agent | at 25° C., 4 months | at 25° C., 6 months | at 10° C., 1 year |
| 21 | NaCl | 97.7 | 96.4 | 97.6 |
| 22 | mannitol | 97.4 | 97.1 | 96.7 |

Oxidized G-CSF at methionine residues was below detection limit in both sample Nos. 21 and 22.

These results showed that good stability could be ensured irrespective of the type of isotonizing agent.

The invention claimed is:

1. A prefilled syringe containing a solution formulation comprising G-CSF which is substantially free from proteins as a stabilizer but which contains histidine or a salt thereof as a stabilizer, and which further contains methionine,
   wherein said histidine or a salt thereof is present at a concentration of from 0.01% (w/v) to 10% (w/v) of total composition, wherein said formulation has oxidized G-CSF at methionine residues in a content of 1% or less after accelerated testing at 40° C. for two weeks, and wherein histidine and methionine are the only free amino acids in the formulation.

2. The prefilled syringe of claim 1, wherein the G-CSF solution formulation further comprises mannitol and/or sodium chloride.

3. The prefilled syringe of claim 1, wherein the G-CSF solution formulation further comprises a surfactant.

4. The prefilled syringe of claim 3 wherein the surfactant is a polyoxyethylene sorbitan alkyl ester.

5. The prefilled syringe of claim 4 wherein the surfactant is Polysorbate 20 and/or 80.

6. The prefilled syringe of claim 1, wherein the G-CSF solution formulation has a pH of 5-7.

7. The prefilled syringe of claim 6, wherein the G-CSF solution formulation has a pH of 5.5-6.8.

8. The prefilled syringe of claim 1, wherein G-CSF is produced from CHO cells.

9. The prefilled syringe according to claim 1, wherein said syringe comprises a glass vial, a stopper and a plunger, wherein said stopper comprises an elastomer.

10. The prefilled syringe according to claim 1, wherein said methionine is present at a concentration of from 0.01% (w/v) to 1% (w/v).

11. The prefilled syringe according to claim 1, wherein said histidine or a salt thereof is present at a concentration of from 0.1% (w/v) to 2% (w/v).

12. The prefilled syringe according to claim 1, wherein said histidine or a salt thereof is present at a concentration of from 0.1% (w/v) to 2% (w/v) and said methionine is present at a concentration of from 0.01% (w/v) to 1% (w/v).

13. The prefilled syringe according to claim 1, wherein said G-CSF maintains at least about 97.2% activity when incubated at 40° C. for two weeks.

14. The prefilled syringe according to claim 12, wherein said G-CSF maintains at least about 97.2% activity when incubated at 40° C. for two weeks.

15. The prefilled syringe according to claim 1, wherein said histidine or a salt thereof is present at a concentration of 0.4% (w/v) and said methionine is present at a concentration of 0.1% (w/v).

16. The prefilled syringe according to claim 15, wherein said G-CSF maintains at least about 99.1% activity when incubated at 40° C. for two weeks, or maintains at least about 97.9% activity when incubated at 25° C. for 6 months, or maintains at least about 98.1% activity when incubated at 10° C. for 1 year.

17. The prefilled syringe according to claim 1, wherein the oxidized G-CSF content in said formulation is determined by reverse phase high-speed liquid chromatography, and wherein the oxidized G-CSF content is below a detection limit after accelerated testing at 40° C. for two weeks.

18. A method for stabilizing a G-CSF solution formulation in the form of a prefilled syringe formulation, comprising:

forming a solution comprising G-CSF, histidine or a salt thereof as a stabilizer and methionine, wherein said solution is substantially free from proteins as a stabilizer, and wherein said histidine or a salt thereof is present at a concentration of from 0.01% (w/v) to 10% (w/v) of total composition, and filling a disposable syringe with said formulation, wherein said formulation has oxidized G-CSF at methionine residues in a content of 1% or less after accelerated testing at 40° C. for two weeks, and wherein histidine and methionine are the only free amino acids in the formulation.

19. The method according to claim 18, wherein said histidine or a salt thereof is present at a concentration of from 0.1% (w/v) to 2% (w/v) and said methionine is present at a concentration of from 0.01% (w/v) to 1% (w/v).

20. The method according to claim 18, wherein said G-CSF maintains at least about 97.2% activity when incubated at 40° C. for two weeks.

21. The method according to claim 19, wherein said G-CSF maintains at least about 97.2% activity when incubated at 40° C. for two weeks.

22. The method according to claim 18, wherein the oxidized G-CSF content in said formulation is determined by reverse phase high-speed liquid chromatography, and wherein the oxidized G-CSF content is below a detection limit after accelerated testing at 40° C. for two weeks.

23. A process for the preparation of a stabilized G-CSF solution formulation in the form of a prefilled syringe formulation, comprising adding histidine or a salt thereof and methionine to the formulation, wherein said histidine or a salt thereof is added at a concentration of from 0.01% (w/v) to 10% (w/v) of total composition, wherein said formulation has oxidized G-CSF at methionine residues in a content of 1% or less after accelerated testing at 40° C. for two weeks, and wherein histidine and methionine are the only free amino acids in the formulation.

24. The process according to claim 23, wherein said histidine or a salt thereof is added at a concentration of from 0.1% (w/v) to 2% (w/v) and said methionine is added at a concentration of from 0.01% (w/v) to 1% (w/v).

25. The process according to claim 23, wherein said G-CSF maintains at least about 97.2% activity when incubated at 40° C. for two weeks.

26. The process according to claim 24, wherein said G-CSF maintains at least about 97.2% activity when incubated at 40° C. for two weeks.

27. The process according to claim 20, wherein the oxidized G-CSF content in said formulation is determined by reverse phase high-speed liquid chromatography, and wherein the oxidized G-CSF content is below a detection limit after accelerated testing at 40° C. for two weeks.

28. A prefilled syringe containing a solution formulation comprising G-CSF and an amino acid stabilizer, wherein said amino acid stabilizer consists of histidine or a salt thereof and methionine, wherein said histidine or a salt thereof is present at a concentration of from 0.01% (w/v) to 10% (w/v) of total composition, wherein no more than 1% of said G-CSF is oxidized at methionine residues when incubated at 40° C. for two weeks, and wherein histidine and methionine are the only free amino acids in the formulation.

29. The prefilled syringe according to claim 28, wherein said histidine or a salt thereof is present at a concentration of from 0.1% (w/v) to 2% (w/v) and said methionine is present at a concentration of from 0.01% (w/v) to 1% (w/v).

30. The prefilled syringe according to claim 28, wherein said G-CSF maintains at least about 97.2% activity when incubated at 40° C. for two weeks.

31. The prefilled syringe according to claim 29, wherein said G-CSF maintains at least about 97.2% activity when incubated at 40° C. for two weeks.

32. The prefilled syringe according to claim 28, wherein an oxidized G-CSF content in said formulation is determined by reverse phase high-speed liquid chromatography, and wherein the oxidized G-CSF content is below a detection limit after accelerated testing at 40° C. for two weeks.

33. A prefilled syringe containing a solution formulation comprising G-CSF which is substantially free from proteins as a stabilizer but which contains histidine or a salt thereof as a stabilizer, and which further contains methionine, and wherein said syringe has a stopper, said stopper comprising an elastomer,
   wherein said histidine or a salt thereof is present at a concentration of from 0.01% (w/v) to 10% (w/v) of total composition,
   wherein no more than 1% of said G-CSF is oxidized at methionine residues when incubated at 40° C. for two weeks, and
   wherein histidine and methionine are the only free amino acids in the formulation.

34. The prefilled syringe according to claim 33, wherein said methionine is present at a concentration of from 0.01% (w/v) to 1% (w/v).

35. The prefilled syringe according to claim 33, wherein said histidine or a salt thereof is present at a concentration of from 0.1% (w/v) to 2% (w/v).

36. The prefilled syringe according to claim 33, wherein said histidine or a salt thereof is present at a concentration of from 0.1% (w/v) to 2% (w/v) and said methionine is present at a concentration of from 0.01% (w/v) to 1% (w/v).

37. The prefilled syringe according to claim 33, wherein said G-CSF maintains at least about 97.2% activity when incubated at 40° C. for two weeks.

38. The prefilled syringe according to claim 36, wherein said G-CSF maintains at least about 97.2% activity when incubated at 40° C. for two weeks.

39. The prefilled syringe according to claim 33, wherein said histidine or a salt thereof is present at a concentration of 0.4% (w/v) and said methionine is present at a concentration of 0.1% (w/v).

40. The prefilled syringe according to claim 39, wherein said G-CSF maintains at least about 99.1% activity when incubated at 40° C. for two weeks, or maintains at least about 97.9% activity when incubated at 25° C. for 6 months, or maintains at least about 98.1% activity when incubated at 10° C. for 1 year.

41. The prefilled syringe according to claim 33, wherein an oxidized G-CSF content in said formulation is determined by reverse phase high-speed liquid chromatography, and wherein the oxidized G-CSF content is below a detection limit after accelerated testing at 40° C. for two weeks.

* * * * *

UNITED STATES PATENT AND TRADEMARK OFFICE
CERTIFICATE OF CORRECTION

| | |
|---|---|
| PATENT NO. | : 7,998,929 B2 |
| APPLICATION NO. | : 10/362921 |
| DATED | : August 16, 2011 |
| INVENTOR(S) | : Yasushi Sato |

It is certified that error appears in the above-identified patent and that said Letters Patent is hereby corrected as shown below:

On the Title Page, at item (54), and at the top of column 1, correct the title of the invention to read as follows:

--SOLUTION FORMULATIONS HAVING LONG-TERM STABILITY--.

On the Title Page, at item (73), Assignee, change "Chugai Seikyaku Kabushiki Kaisha, Tokyo (JP)" to read: --Chugai Seiyaku Kabushiki Kaisha, Tokyo (JP)--.

Signed and Sealed this
Twenty-seventh Day of December, 2011

David J. Kappos
*Director of the United States Patent and Trademark Office*